(12) United States Patent
Zhang et al.

(10) Patent No.: US 11,161,817 B2
(45) Date of Patent: Nov. 2, 2021

(54) QUINOLINE DERIVATIVE AND USE THEREOF AS TYROSINE KINASE INHIBITOR

(71) Applicants: CHONGQING PHARMACEUTICAL INDUSTRIAL RESEARCH INSTITUTE CO. LTD., Chongqing (CN); YAOPHARMA CO., LTD., Chongqing (CN)

(72) Inventors: Yang Zhang, Shanghai (CN); Zhengxia Chen, Shanghai (CN); Meibi Dai, Shanghai (CN); Wenju Li, Shanghai (CN); Jian Li, Shanghai (CN); Shuhui Chen, Shanghai (CN)

(73) Assignees: CHONGQING PHARMACEUTICAL INDUSTRIAL RESEARCH INSTITUTE CO. LTD., Chongqing (CN); YAOPHARMA CO., LTD., Chongqing (CN)

( * ) Notice: Subject to any disclaimer, the term of this patent is extended or adjusted under 35 U.S.C. 154(b) by 0 days.

(21) Appl. No.: 16/651,521

(22) PCT Filed: Sep. 20, 2018

(86) PCT No.: PCT/CN2018/106674
§ 371 (c)(1),
(2) Date: Mar. 27, 2020

(87) PCT Pub. No.: WO2019/062637
PCT Pub. Date: Apr. 4, 2019

(65) Prior Publication Data
US 2020/0262791 A1 Aug. 20, 2020

(30) Foreign Application Priority Data

Sep. 28, 2017 (CN) .......................... 201710900497.6
Jul. 5, 2018 (CN) .......................... 201810732319.1

(51) Int. Cl.
*C07D 215/48* (2006.01)
(52) U.S. Cl.
CPC .................... *C07D 215/48* (2013.01)
(58) Field of Classification Search
CPC .................................................... C07D 215/48
See application file for complete search history.

(56) References Cited

U.S. PATENT DOCUMENTS

| 10,654,808 B2* | 5/2020 | Long ................ C07D 471/04 |
| 2014/0057908 A1 | 2/2014 | Smith et al. |
| 2014/0179736 A1 | 6/2014 | Schwab et al. |
| 2019/0119217 A1 | 4/2019 | Long et al. |

FOREIGN PATENT DOCUMENTS

| CN | 1308310 C | 4/2007 |
| CN | 101311166 A | 11/2008 |
| CN | 103391773 A | 11/2013 |
| CN | 103717221 A | 4/2014 |
| CN | 106046007 A | 10/2016 |
| CN | 109134365 A | 1/2019 |
| EP | 1415987 A1 | 5/2004 |
| WO | WO-2006090163 A1 | 8/2006 |

OTHER PUBLICATIONS

Mar. 26, 2019 Chinese Office Action issued in Chinese Patent Application No. 2018111402798 and Search Report.
SONG et.al., "Advances in Research of Small Molecule Tyrosine Kinase Inhibitors for Targeted Cancer Therapy", Chin Pharm J, Feb. 2016, vol. 51, No. 3, 165-171.
Extended European Search report issued for corresponding application EP18862179.1 dated Jul. 21, 2020.

* cited by examiner

*Primary Examiner* — Timothy R Rozof
(74) *Attorney, Agent, or Firm* — Harness, Dickey & Pierce, P.L.C.

(57) ABSTRACT

A quinoline derivative compound shown in formula (II), a pharmaceutically acceptable salt thereof, and an application of the same in preparing a drug for treating a disease related to a tyrosine kinase inhibitor.

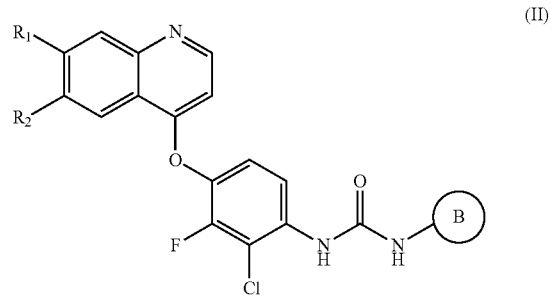

9 Claims, No Drawings

QUINOLINE DERIVATIVE AND USE THEREOF AS TYROSINE KINASE INHIBITOR

CROSS-REFERENCE TO RELATED APPLICATIONS

This application is a 371 National Phase of International Application No. PCT/CN2018/106674, filed Sep. 20, 2018, which claims the benefit of Chinese Patent Application No. CN 201710900497.6, filed Sep. 28, 2017 and Chinese Patent Application No. CN 201810732319.1, filed Jul. 5, 2018. The entire disclosures of the above applications are incorporated herein by reference.

FIELD OF THE INVENTION

The present disclosure relates to a quinoline derivative and a use thereof in manufacturing a medicament for treating a disease associated with tyrosine kinase inhibitor. Specifically, the present disclosure relates to a compound represented by formula (II) and a pharmaceutically acceptable salt thereof.

PRIOR ARTS

Protein tyrosine kinase (PTK) is an enzyme, which in conjunction with ATP as a substrate phosphorylates tyrosine residues in peptides and proteins. These enzymes are key factors in the regulation of cell signaling, such as cell proliferation and differentiation. Particularly, the PTK also includes receptor tyrosine kinases, which include hepatocyte growth factor (HGF), platelet-derived growth factor (PDGF), and kinases (FGF and VEGF) that play a role in angiogenesis; and, in addition, non-receptor tyrosine kinases, which include LCK, ABL, etc.

c-Met protein (also known as the hepatocyte growth factor (HGF) receptor) is a transmembrane 190 kDa heterodimer with tyrosine kinase activity, encoded by c-Met oncogene. The HGF/c-Met signaling pathway has been demonstrated to be associated with a variety of cellular responses, including mitogenic activity, proliferation activity, morphogenic activity, and angiogenic activity. Inhibitors of the HGF/c-Met pathway have significant potential for treating cancer.

ABL is a tyrosine kinase encoded by a proto-oncogene. The activated ABL can promote cell proliferation, differentiation, EMT, etc. In hematologic neoplasms, it is activated mainly by gene fusion such as BCR-ABL. In solid tumors, it is activated mainly by gene amplification, overexpression, and upstream receptor tyrosine kinases such as PDGFR, EGFR, etc. TNIK is a serine/threonine kinase, which can bind to 3-catenin/TCF in Wnt signaling pathway, activate downstream target genes of Wnt signal and promote tumor growth. MINK is a member of the STE20 protein kinase family. It is highly expressed in the central nervous system and can activate JNK and p38 signaling pathways.

FGFR is a type of biological active substances that have functions of transmitting biological signals, regulating cell growth, participating in tissue repair, etc. In recent years, many members of the FGFR family have been found to play important roles in tumorigenesis and development process. Fibroblast growth factor receptor (FGFR) is a type of receptor proteins that can specifically bind to fibroblast growth factor (FGF). The FGFRs family includes the following types: FGFR1b, FGFR1c, FGFR2b, FGFR2c, FGFR3b, FGFR3c and FGFR4. The FGFs binding to different subtypes of FGFR are not the same. The binding of FGFs and FGFRs results in the autophosphorylation of multiple tyrosine residues in the cells. Phosphorylated FGFRs activate downstream signaling pathways including MEK/MAPK, PLCy/PKC, PI3K/AKT, STATS, etc. FGFR4 is highly expressed in liver cancer, colon cancer, gastric cancer, esophageal cancer and testicular cancer, and FGF19 that specifically binds to FGFR4 is highly expressed in human colon, liver and lung cancer cells. The abnormal signals of the specific binding of FGFR4s and FGF19 are important factors of multiple tumorigenesis and metastasis.

Vascular endothelial cell growth factor (VEGF) and platelet-derived growth factor (PDGF) play an important role in tumor neovascularization. They bind to their receptors VEGFR and PDGFR, transmit signals to the intracellular region, then undergo phosphorylation dimerization, and activate this signal pathway and transfer energy downstream, resulting in uncontrolled growth, metastasis, and proliferation of tumor cells.

As for the treatment of tumor cells, the above several targets such as ABL, C-Met, TNIK, FGFR1-4, VEGFR (FLT1, KDR, FLT4) and PDGFR can cooperate with and complement each other, reduce the escape of tumor cells, reduce drug resistance and improve therapeutic effect in the molecular action mechanism, therefore, the drugs that can act on these targets at the same time are greatly anticipated.

At present, the commercially available multi-kinase inhibitor Lovatinib, which has ABL, TNIK, FGFR, VEGFR, and PDGFR activities simultaneously, exhibits an excellent performance in clinical treatment and has a high response rate in patients.

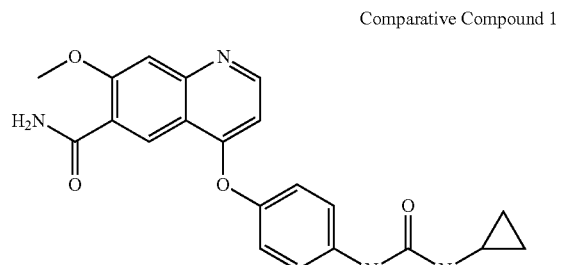

(Lovatinib)

Comparative Compound 1

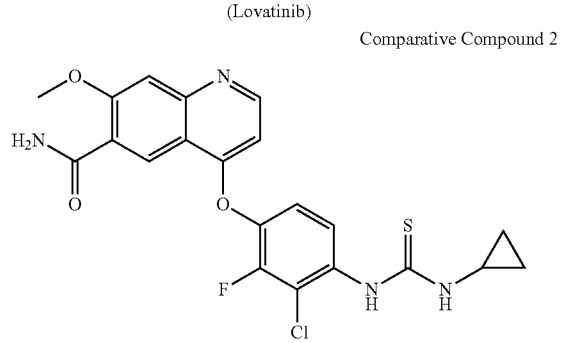

Comparative Compound 2

Content of the Invention

The present disclosure provides a compound represented by formula (II) or a pharmaceutically acceptable salt thereof,

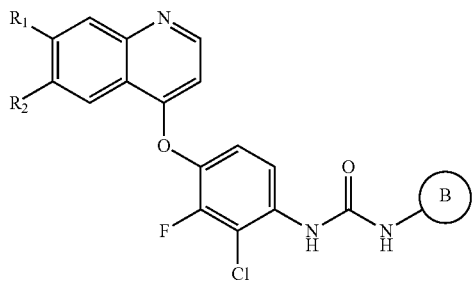

(II)

wherein, $R_1$ is selected from $C_{1-6}$ alkoxy optionally substituted by 1, 2 or 3 R;

$R_2$ is selected from —C(=O)NH$_2$ and —C(=O)NH—C$_{1-3}$ alkyl;

ring B is selected from $C_{3-6}$ cycloalkyl;

R is selected from F, Cl, Br, I, OH and NH$_2$.

In some embodiments of the present disclosure, $R_1$ is

and the other variables are as defined in the present disclosure.

In some embodiments of the present disclosure, $R_2$ is —C(=O)NH$_2$, and the other variables are as defined in the present disclosure.

In some embodiments of the present disclosure, ring B is cyclopropyl, and the other variables as defined in the present disclosure.

The present disclosure provides a compound represented by formula (I) or a pharmaceutically acceptable salt thereof,

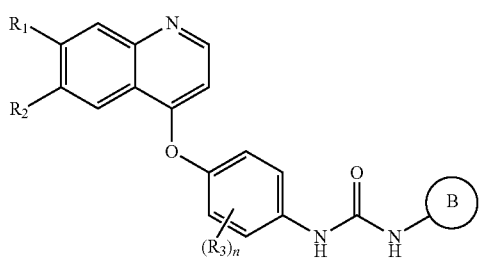

(I)

wherein, $R_1$ is selected from $C_{1-6}$ alkoxy optionally substituted by 1, 2 or 3 R;

$R_2$ is selected from —C(=O)NH$_2$ and —C(=O)NH—C$_{1-3}$ alkyl;

$R_3$ is selected from H, F, Cl, Br, I, OH and NH$_2$;

ring B is selected from $C_{3-6}$ cycloalkyl;

n is selected from 2 and 3;

R is selected from F, Cl, Br, I, OH and NH$_2$.

In some embodiments of the present disclosure, $R_1$ is

and the other variables are as defined in the present disclosure.

In some embodiments of the present disclosure, $R_2$ is —C(=O)NH$_2$, and the other variables are as defined in the present disclosure.

In some embodiments of the present disclosure, $R_3$ is selected from F and Cl, and the other variables are as defined in the present disclosure.

In some embodiments of the present disclosure, ring B is cyclopropyl, and the other variables are as defined in the present disclosure.

In some embodiments of the present disclosure, n is 2, and the other variables are as defined in the present disclosure.

The present disclosure also has some embodiments obtained by arbitrary combination of the above variables.

In some embodiments of the present disclosure, the compound or the pharmaceutically acceptable salt thereof is selected from

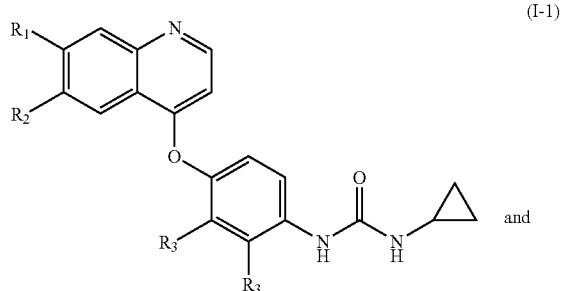

(I-1)

and

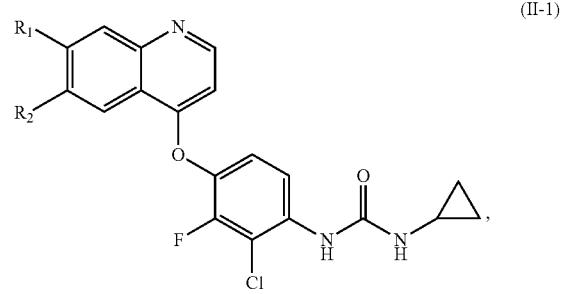

(II-1)

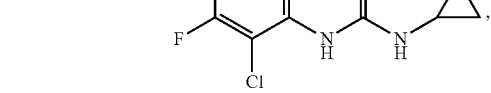

wherein, $R_1$, $R_2$, and $R_3$ are as defined in the present disclosure.

The present disclosure also provides the following compound:

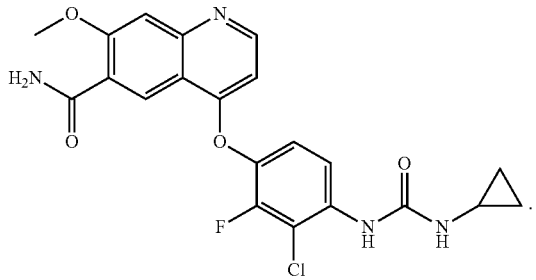 [SMILES: COc1cc2nccc(Oc3ccc(NC(=O)NC4CC4)c(Cl)c3F)c2cc1C(N)=O]

The present disclosure also provides a pharmaceutical composition comprising a therapeutically effective amount of the compound or the pharmaceutically acceptable salt thereof as an active ingredient, and a pharmaceutically acceptable carrier.

The present disclosure also provides a use of the compound or the pharmaceutically acceptable salt thereof or the composition in manufacturing a medicament for treating a disease associated with tyrosine kinase inhibitor.

In some embodiments of the present disclosure, in the use, the disease associated with tyrosine kinase inhibitor refers to tumor disease and immune disorder.

Definition and Description

Unless otherwise indicated, the following terms and phrases used herein are intended to have the following meanings. A specific term or phrase should not be considered indefinite or unclear in the absence of a particular definition, but should be understood in its ordinary sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, and commensurate with a reasonable benefit/risk ratio.

The term "pharmaceutically acceptable salt" refers to a salt of the compound of the present disclosure which is prepared from the compound having a specific substituent of the present disclosure and a relatively non-toxic acid or base. When the compound of the present disclosure contains a relatively acidic functional group, a base addition salt can be obtained by contacting a sufficient amount of base with the neutral form of the compound in a pure solution or a suitable inert solvent. The pharmaceutically acceptable base addition salt include a salt of sodium, potassium, calcium, ammonium, organic amine or magnesium, or similar salts. When the compound of the present disclosure contains a relatively basic functional group, an acid addition salt can be obtained by contacting a sufficient amount of acid with the neutral form of the compound in a pure solution or a suitable inert solvent. Examples of the pharmaceutically acceptable acid addition salt include inorganic acid salts, wherein the inorganic acids include, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; organic acid salts, wherein the organic acids include, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, methanesulfonic acid and similar acids; and salts of an amino acid (such as arginine, and the like), and salts of an organic acid such as glucuronic acid. Certain specific compounds of the present disclosure that contain both basic and acidic functional groups can be converted to any base or acid addition salt.

The pharmaceutically acceptable salt of the present disclosure can be synthesized from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

Some compounds of the present disclosure may exist in unsolvated or solvated forms, including hydrated forms. Generally speaking, the solvated form is equivalent to the unsolvated form, and both are included within the scope of the present disclosure.

The compounds of the disclosure may exist in specific geometric or stereoisomeric forms. The present disclosure contemplates all such compounds, including cis- and trans-isomers, (−)- and (+)-enantiomers, (R)- and (S)-enantiomers, diastereomers, (D)-isomers, (L)-isomers, and racemic and other mixtures thereof, such as enantiomers or diastereomers enriched mixtures, all of which are within the scope of the disclosure. Additional asymmetric carbon atoms may be present in substituents such as alkyl. All these isomers and their mixtures are included within the scope of the present disclosure.

Unless otherwise indicated, the terms "enantiomers" or "optical isomers" refer to stereoisomers which are mirror images of each other.

Unless otherwise indicated, the terms "cis/trans-isomer" or "geometric isomer" are caused by the inability of a double bond or a single bond of a ring-forming carbon atom to rotate freely.

Unless otherwise indicated, the term "diastereomer" refers to a stereoisomer in which a molecule has two or more chiral centers, and there is non-mirror image relationship between molecules.

Unless otherwise indicated, "(D)" or "(+)" means dextrorotation, "(L)" or "(−)" means levorotation, and "(DL)" or "(±)" means racemization.

Unless otherwise indicated, a wedged solid bond () and a wedged dashed bond () represent the absolute configuration of a stereocenter, a straight solid bond () and a straight dashed bond () represent the relative configuration of a stereocenter, a wave line () represents a wedged solid bond () or a wedged dashed bond (), or a wave line () represents a straight solid bond () or a straight dashed bond ().

The compounds of the disclosure may be specific. Unless otherwise indicated, the term "tautomer" or "tautomeric form" means that at room temperature, the isomers of different functional groups are in dynamic equilibrium and can be quickly converted to each other. If tautomer is possible (e.g. in solution), the chemical equilibrium of the tautomer can be reached. For example, proton tautomer (also known as prototropic tautomer) include interconversions via proton migration, such as keto-enol isomerization and imine-enamine isomerization. Valence tautomer includes interconversion formed by recombination of some bonding electrons. A specific example of the keto-enol tautomerization is the interconversion between two tautomers of pentane-2,4-dione and 4-hydroxypent-3-en-2-one.

Unless otherwise indicated, the term "enriched in an isomer", "isomer enriched", "enriched in an enantiomer" or "enantiomer enriched" refers to that the content of the isomer or enantiomer is less than 100%, and the content of the isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or more 99.9%.

Unless otherwise indicated, the terms "isomer excess" or "enantiomer excess" refer to the difference between the relative percentages of two isomers or two enantiomers. For example, if the content of one isomer or enantiomer is 90%, and the content of the other isomer or enantiomer is 10%, the isomer or enantiomeric excess (ee value) is 80%.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine). The compounds of the present disclosure may contain atomic isotopes in unnatural proportions on one or more of the atoms constituting the compound. For example, the compound can be radiolabeled with a radioactive isotope, such as tritium ($^3$H), iodine-125 ($^{125}$I) or C-14 ($^{14}$C). As another example, deuterated drugs can be obtained by replacing hydrogen by deuterium. The bond between deuterium and carbon is stronger than the bond between ordinary hydrogen and carbon. Compared with non-deuterated drugs, deuterated drugs have the advantages of reduced toxic and side effects, increased drug stability, enhanced efficacy, prolonged biological half-life of drugs, and the like. Transformations of all isotopic compositions of the compounds of the present disclosure, whether radioactive or not, are included within the scope of the disclosure.

For a drug or a pharmacological active agent, the term "effective amount" or "therapeutically effective amount" refers to a sufficient amount of a drug or agent that is non-toxic but is capable of achieving the desired effect. For an oral dosage form in the present disclosure, the "effective amount" of an active substance in the composition refers to the amount required to achieve the desired effect when used in combination with another active substance in the composition. The determination of an effective amount varies from person to person, depends on the age and general situation of the receptor, and the specific active substance. The appropriate effective amount in a case can be determined by those skilled in the art based on routine tests.

The terms "active ingredient", "therapeutic agent", "active substance" or "active agent" refer to a chemical entity that can effectively treat a target disorder, disease or condition.

"Optional" or "optionally" means that the subsequent event or condition may occur but not requisite, that the term includes the instance in which the event or condition occurs and the instance in which the event or condition does not occur.

The term "substituted" means any one or more hydrogen atoms on a specific atom are substituted by a substituent, including deuterium and hydrogen variants, as long as the valence of the specific atom is normal and the substituted compound is stable. When the substituent is oxygen (i.e. =O), it means two hydrogen atoms are substituted. Oxygen substitution does not occur on aromatic groups. The term "optionally substituted" means an atom can be substituted by a substituent or not, unless otherwise indicated, the species and number of the substituent may be arbitrary as long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When the enumerative linking group does not indicate the direction for linking, the direction for linking is arbitrary, for example, the linking group L contained in

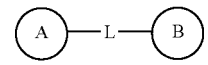

is -M-W—, then -M-W— can link ring A and ring B to form

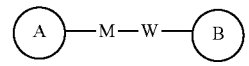

in the direction same as left-to-right reading order, and form

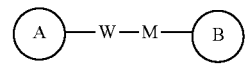

in the direction contrary to left-to-right reading order. Combinations of the linking groups, substituents and/or variants thereof are permissible only if such combinations result in stable compounds.

Unless otherwise indicated, the term "hetero" means heteroatoms or heteroatomic groups (i.e. atomic groups containing heteroatoms), including atoms other than carbon (C) and hydrogen (H), and atomic groups containing these heteroatoms, such as oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)—, or —S(=O)N(H)—.

Unless otherwise indicated, "ring" means a substituted or unsubstituted cycloalkyl, heterocycloalkyl, cycloalkenyl, heterocycloalkenyl, cycloalkynyl, heterocycloalkynyl, aryl or heteroaryl. The ring includes a single ring, a linked ring, a spiro ring, a fused ring or a bridged ring. The number of the atom on the ring is usually defined as the member number of the ring, for example, a "5- to 7-membered ring" means that 5 to 7 atoms are arranged on a ring. Unless otherwise indicated, the ring optionally contains 1 to 3 heteroatoms. Therefore, a "5- to 7-membered ring" includes, for example, phenyl, pyridinyl and piperidinyl; on the other hand, the term "5- to 7-membered heterocycloalkyl ring" includes pyridyl and piperidinyl, but excluding phenyl. The term "ring" also includes a ring system containing at least one ring, wherein each ring independently meets the above definition.

Unless otherwise indicated, the term "hydrocarbyl" or its hyponyms (e.g., alkyl, alkenyl, alkynyl, and aryl, etc.), by itself or as part of another substituent, refers to a linear, branched chain or cyclic hydrocarbon radical or combination thereof, they can be fully saturated (e.g., alkyl), mono- or polyunsaturated (e.g., alkenyl, alkynyl, and aryl), can be mono-, di- or poly-substituted, can be monovalent (e.g., methyl), divalent (e.g., methylene) or multivalent (e.g., methenyl), can also include a divalent or multivalent group, have a specified number of carbon atom (for example, $C_1$-$C_{12}$ indicates 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes, but is not limited to, aliphatic hydrocarbyl and aromatic hydrocarbyl, the aliphatic hydrocarbyl includes linear and cyclic hydrocarbyl, specifically includes but not limited to alkyl, alkenyl, and alkynyl. The aromatic hydrocarbyl includes but is not limited to 6- to 12-membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl, tert-butyl, isobutyl, sec-butyl, cyclohexyl, (cyclohexyl)methyl, cyclopropylmethyl, and the homologues or isomers of n-pentyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and higher homologues and isomers.

Unless otherwise indicated, the term "heterohydrocarbyl" or its hyponyms (such as heteroalkyl, heteroalkenyl, heteroalkynyl, heteroaryl, etc.) by itself or in combination with another term refers to a stable linear, branched chain or a cyclic hydrocarbon group or a combination thereof, consisting of a certain number of carbon atoms and at least one heteroatom. In some embodiments, the term "heteroalkyl", by itself, or in combination with another term, refers to a stable linear or branched chain hydrocarbon group or a combination thereof, having a certain number of carbon atoms and at least one heteroatom. In a typical embodiment, the heteroatoms are selected from B, O, N, and S, wherein nitrogen and sulfur atoms are optionally oxidized, and nitrogen heteroatom is optionally quaternized. A heteroatom or heteroatomic group can be located at any internal position of the heterohydrocarbyl, including the position where the hydrocarbyl is attached to the rest of the molecule, but the terms "alkoxy", "alkamino" and "alkylthio" (or thioalkoxy) are conventional expressions and refer to those alkyl groups that are connected to the rest of the molecule through an oxygen atom, amino, or sulfur atom, respectively. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. Up to two heteroatoms may be continuous, such as —$CH_2$—NH—$OCH_3$.

Unless otherwise indicated, the term "cyclohydrocarbyl", "heterocyclohydrocarbyl" or its hyponyms (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g., heteroalkyl, and heterocycloalkyl), one heteroatom can occupy the position where the heterocycle attaches to the remaining position of the molecule. Examples of the cyclohydrocarbyl include, but are not limited to, cyclopentyl, cyclohexyl, 1-cyclohexenyl, 3-cyclohexenyl, cycloheptyl and the like. Non-limiting examples of heterocyclyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran indol-3-yl, tetrahydrothiophen-2-yl, tetrahydrothiophen-3-yl, 1-piperazinyl and 2-piperazinyl.

Unless otherwise indicated, the term "alkyl" refers to a linear chain or branched saturated hydrocarbyl, can be mono-substituted (e.g., —$CH_2F$) or poly-substituted (e.g., —$CF_3$), can be monovalent (e.g., methyl), divalent (e.g., methylene) or multivalent (e.g., methenyl). Examples of alkyl include methyl (Me), ethyl (Et), propyl (such as n-propyl and isopropyl), butyl (such as n-butyl, isobutyl, s-butyl, tert-butyl), pentyl (such as n-pentyl, isopentyl, neopentyl) and the like.

Unless otherwise indicated, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornyl, [2.2.2] bicyclooctane, [4.4.0]bicyclodecane, and the like.

Unless otherwise indicated, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo($C_1$-$C_4$)alkyl" is meant to include, but not limited to, trifluoromethyl, 2,2,2-trifluoroethyl, 4-chlorobutyl, 3-bromopropyl and the like.

Unless otherwise indicated, examples of haloalkyl include, but are not limited to trifluoromethyl, trichloromethyl, pentafluoroethyl and pentachloroethyl.

"Alkoxy" represents the above-mentioned alkyl having a specific number of carbon atoms linked by an oxygen bridge. Unless otherwise indicated, $C_{1-6}$ alkoxy includes $C_1$, $C_2$, $C_3$, $C_4$, $C_5$ and $C_6$ alkoxy. Examples of alkoxy include, but are not limited to, methoxy, ethoxy, n-propoxy, isopropoxy, n-butoxy, sec-butoxy, t-butoxy, n-pentoxy and S-pentyloxy.

The term "leaving group" refers to a functional group or atom that can be replaced by another functional group or atom through a substitution reaction (e.g., an affinity substitution reaction). For example, representative leaving groups include triflate; chlorine, bromine, and iodine; sulfonate group such as mesylate, tosylate, p-bromobenzenesulfonate, and p-toluenesulfonate, and the like; acyloxy, such as acetoxy, trifluoroacetoxy, and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl;

acyl, such as alkanoyl (e.g, acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g, acetyl); arylmethyl such as benzyl (Bn), p-methoxybenzyl (PMB), 9-fluorenylmethyl (Fm), and diphenylmethyl (DPM); silyl such as trimethylsilyl (TMS) and tert-butyl dimethyl silyl (TBS) and the like.

The compounds of the present disclosure can be prepared by a variety of synthetic methods well known to those skilled in the art, including the following enumerative embodiment, the embodiment formed by the following enumerative embodiment in combination with other chemical synthesis methods and the equivalent replacement well known to those skilled in the art. The preferred embodiments include, but are not limited to, the embodiments of the present disclosure.

The solvent used in the present disclosure is commercially available. The present disclosure employs the following abbreviations: aq stands for water; HATU stands for O-(7-azabenzotriazol-1-yl)-N,N,N',N'-tetramethyluronium hexafluorophosphate; EDC stands for N-(3-dimethylaminopropyl)-N'-ethylcarbodiimide hydrochloride; m-CPBA stands for 3-chloroperoxybenzoic acid; eq stands for equivalent; CDI stands for carbonyldiimidazole; DCM stands for dichloromethane; PE stands for petroleum ether; DIAD stands for diisopropyl azodicarboxylate; DMF stands for N,N-dimethylformamide; DMSO stands for dimethyl sulfoxide; EtOAc stands for ethyl acetate, EtOH stands for ethanol; MeOH stands for methanol; CBz stands for benzyloxycarbonyl, which is an amine protecting group; BOC stands for tert-butoxycarbonyl, which is an amine protecting group; HOAc stands for acetic acid; NaCNBH$_3$ stands for sodium cyanoborohydride; r.t. stands for room temperature; O/N stands for overnight; THF stands for tetrahydrofuran; Boc$_2$O stands for di-tert-butyldicarbonate; TFA stands for trifluoroacetic acid; DIPEA stands for diisopropylethylamine; SOCl$_2$ stands for thionyl chloride, CS$_2$ stands for carbon disulfide; TsOH stands for p-toluenesulfonic acid; NFSI stands for N-fluoro-N-(phenyl sulfonyl)benzenesulfonamide; NCS stands for 1-chloropyrrolidine-2,5-dione; n-Bu$_4$NF stands for tetrabutylammonium fluoride; iPrOH stands for 2-propanol; mp stands for melting point; LDA stands for lithium diisopropylamide; EDCI stands for 1-(3-dimethylaminopropyl)-3-ethylcarbodiimide hydrochloride; dppf stands for 1,1'-bis (diphenylphosphine) ferrocene; HATU stands for 2-(7-oxobenzotriazole)-N,N,N',N'-tetramethylurea hexafluophosphate; Ti(i-PrO)$_4$ stands for titanium tetraisopropoxide; NBS stands for N-bromosuccinimide; DAST stands for diethylaminosulfur trifluoride; LiHMDS stands for lithium hexamethyldisilazide, AIBN stands for azodiisobutyronitrile; POCl$_3$ stands for phosphorus oxychloride; PEG400 stands for polyethylene glycol 400; NMP stands for N-methylpyrrolidone; MOPS stands for 3-morpholinopropanesulfoinc acid.

The compounds are named manually or by ChemDraw® software, and commercially available compounds use their vendor directory names.

Technical Effect

Compared with Comparative Compound 1, the compound of the present disclosure not only has the same multi-active targets, but also has a 5 to 10-fold improvement in the activities on targets such as ABL, TNIK, FGFR1, FGFR3, FGFR4 and the like, while introducing a new c-Met activity with IC$_{50}$ value of 100 nM.

Compared with Comparative Compound 2, the compound of the present disclosure has a nearly 70-fold increase in ABL activity and an 8-fold increase in TNIK, which is very significant and unexpected; the compound of the present disclosure with fluorine and chlorine located on the same side of the benzene ring has significantly improved inhibitory activities on FGFR1, FGFR4 and ABL kinases, compared with Comparative Compounds 3, 4, 5, 6, and 7 with fluorine and chlorine located on other positions.

The compound of the present disclosure has better therapeutic effect in cancers with gene fusion such as BCR-ABL and the like; Compound 1B has better tumor treatment effect due to the improvement of the activities on these important targets, especially, the improvement of the activities on FGFR and c-Met, which will result in a better therapeutic effect in patients with gastric cancer, lung cancer and the like with high expression of FGFR and c-Met.

The compound of the present disclosure has lower clearance rate and higher oral bioavailability in mice and rat species, and has excellent druggability.

DETAILED DESCRIPTION OF THE PREFERRED EMBODIMENT

The following embodiments further illustrate the present disclosure, but the present disclosure is not limited thereto. The present disclosure has been described in detail herein, and its specific embodiments are also disclosed. It is obvious for those skilled in the art to make various changes and improvements to the specific embodiments of the present disclosure without departing from the spirit and scope of the present disclosure.

Process A

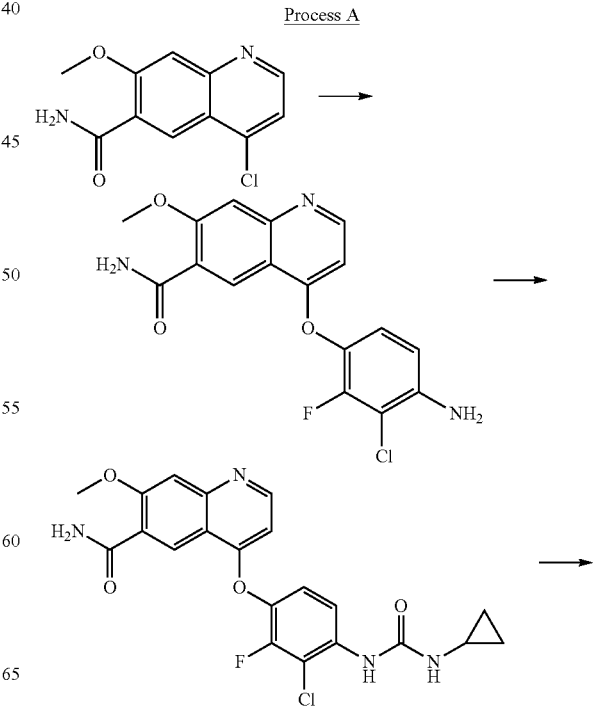

-continued

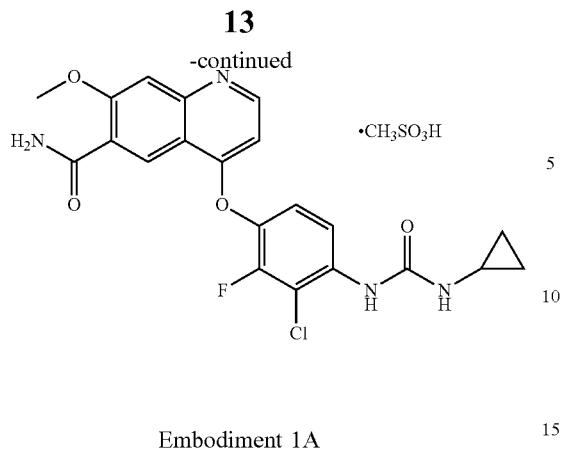

Embodiment 1A

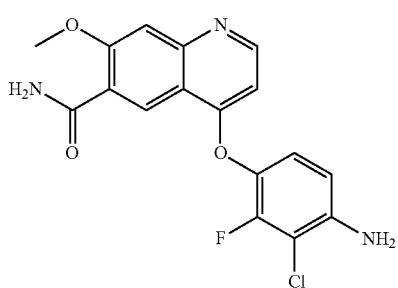 [SMILES: COc1cc2nccc(Oc3ccc(N)c(Cl)c3F)c2cc1C(N)=O]

4-Chloro-7-methoxyquinoline-6-formamide (550.0 g) was added to a reaction kettle at 20-30° C. DMSO (16.5 L) was added to the reaction kettle at 20-30° C. 2-Fluoro-3-chloro-4-aminophenol was added to the reaction kettle at 20-30° C. Sodium tert-butoxide (229 g) was slowly added to the reaction kettle at 20-35° C. under stirring within 10-15 minutes. The reaction kettle was heated for 1.5 hours to 96° C. (internal temperature). The reaction was performed under stirring at 96-100° C. for 6.5 hours, and there was no remainder of 4-amino-3-chloro-2-fluorophenol. The reaction solution was cooled to 20-30° C. 23.1 L water was slowly added to the reaction solution under stirring with dark brown solid precipitated during the process, and the internal temperature was maintained below 40° C. The reaction solution was stirred at 30-40° C. for 0.5 hour, cooled to 20-30° C., and filtered. The filter cake and 3.5 L water was added into a reaction kettle at 20-30° C., stirred at 20-30° C. for 0.5 hour, and filtered. The filter cake and 4.0 L water was added into a reaction kettle at 20-30° C., stirred at 20-30° C. for 0.5 hour, and filtered. The filter cake was dried in a vacuum dryer at 40° C. for 18 hours (with phosphorus pentoxide used as the desiccant and under oil-pump vacuum). The obtained solid was pulverized to obtain 758 g off-white solid, which was further dried at 40° C. for 18 hours (with phosphorus pentoxide used as the desiccant and under oil-pump vacuum) to obtain a product of Embodiment 1A.

LCMS(ESI) m/z: 362.0[M+1]$^+$ $^1$H NMR (400 MHz, DMSO-d$_6$) δ ppm 8.68 (br s, 2H), 7.82-7.96 (m, 1H), 7.67-7.82 (m, 1H), 7.46-7.59 (m, 1H), 7.12-7.26 (m, 1H), 6.67-6.80 (m, 1H), 6.43-6.58 (m, 1H), 5.84 (s, 2H), 4.04 (s, 3H).

Embodiment 1B

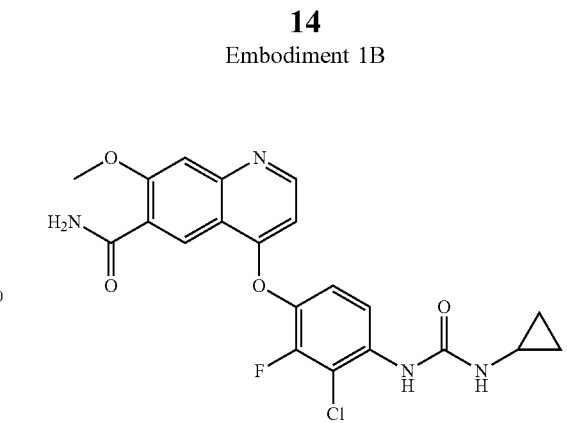

The product of Embodiment 1A (6.05 g) was added to a three-necked flask containing NMP (60 mL). Pyridine (1.32 g) and phenyl chloroformate (5.20 g) were added to the reaction system, the reaction system was stirred at room temperature (25-30° C.) for 1 hour to obtain an intermediate and the reaction was completed. Cyclopropylamine (2.84 g) was added to the reaction system, the reaction solution was stirred at room temperature (25-30° C.) for 0.5 hour, and the reaction was completed. 20 mL ethanol was added to the reaction solution, tap water (500 mL) was added to the reaction system under stirring, and a solid was precipitated therefrom. The mixture was filtered. The filter cake was rotary-evaporated under reduced pressure to obtain a crude product (earth-yellow solid, 5.26 g); the crude product was purified by column chromatography (DCM:MeOH=20/1 to 10/1) to obtain a product (earth-yellow solid, 3.12 g). 4 mL anhydrous ethanol was added to the product and stirred at room temperature for 18 hours, and filtered. The filter cake was washed with 1 mL ethanol, and dried under reduced pressure to obtain a product of Embodiment 1B. 1 equivalent hydrochloric acid, sulfuric acid or methanesulfonic acid was added to the solution of the compound in acetone or ethanol to obtain the corresponding salt.

LCMS (ESI) m/z: 445.0 [M+1]$^+$ $^1$H NMR (400 MHz, DMSO-d$_6$) ppm 8.66-8.71 (m, 2H), 8.12-8.20 (m, 2H), 7.72-7.93 (m, 2H), 7.45 (t, J=9.16 Hz, 1H), 7.28 (d, J=2.76 Hz, 1H), 6.58 (d, J=5.02 Hz, 1H), 4.05 (s, 3H), 2.56-2.64 (m, 1H), 0.38-0.77 (m, 4H).

Embodiment 1

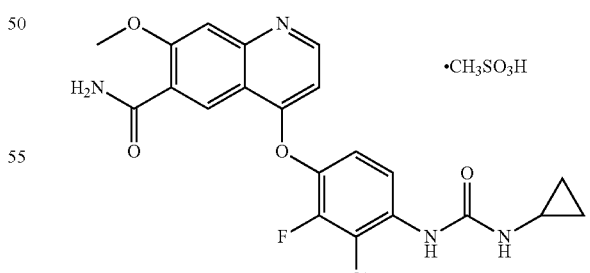

The product of Embodiment 1B (1.5 g, 3.37 mmol) was added to EtOH (45 mL), and the reaction temperature was raised to 60° C. At this temperature, CH$_3$SO$_3$H (324.07 mg, 3.37 mmol, 240.05 μL) was added dropwise to the reaction solution. After the dropwise addition was completed, the reaction solution became clear. The reaction solution was naturally cooled to 15-20° C. under stirring, and stirred at this temperature for 2 hours. A large amount of brown solid was precipitated, filtered, and the filter cake was rinsed with anhydrous ethanol (5 mL). The obtained filter cake was rotary-evaporated under reduced pressure at 50° C. to dryness without purification to obtain a product of Embodiment 1.

LCMS (ESI) m/z: 445.0 [M+1]⁺

¹H NMR (400 MHz, DMSO-d₆) δ ppm 9.02 (d, J=6.53 Hz, 1H) 8.72 (s, 1H) 8.18-8.27 (m, 2H) 7.87-8.03 (m, 2H) 7.65 (s, 1H) 7.53 (t, J=9.03 Hz, 1H) 7.32 (br s, 1H) 7.11 (d, J=6.27 Hz, 1H) 4.08 (s, 3H) 2.55-2.62 (m, 1H) 2.35 (s, 3H) 0.34-0.75 (m, 4H)

Process B

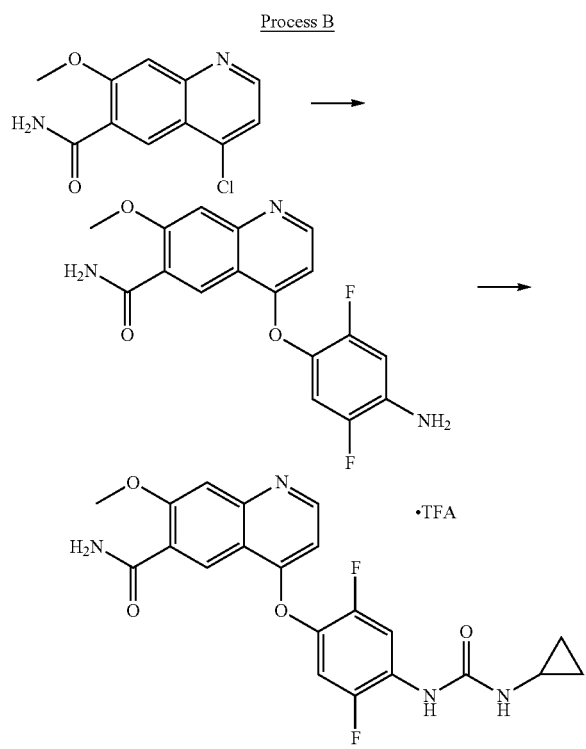

Comparative Embodiment 3A

4-Chloro-7-methoxyquinoline-6-formamide (200 mg, 845.12 μmol), 4-amino-2,5-difluorophenol (184.13 mg, 1.01 mmol) and potassium tert-butoxide (113.80 mg, 1.01 mmol) were added to a microwave tube filled with N-methyl pyrrolidone (5 mL), and then heated to 140° C. under nitrogen atmosphere and reacted under stirring for 1 hour in a microwave synthesizer. The reaction solution was added to 30 mL water and a solid was precipitated. The reaction solution was filtered to obtain a product of Comparative Embodiment 3A. The obtained product was directly used in the next step without purification.

LCMS (ESI) m/z: 346.1 [M+H]⁺

Comparative Embodiment 3

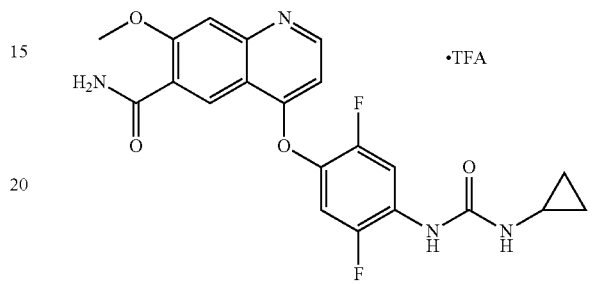

Triphosgene (34.38 mg, 115.84 μmol) was added to the mixture of the product of Comparative embodiment 3A (200 mg, 579.21 μmol) and triethylamine (175.83 mg, 1.74 mmol, 241.86 μL) in dichloromethane (5 mL), and the mixture was stirred under nitrogen atmosphere at 15-20° C. for 15 minutes. Then cyclopropylamine (66.14 mg, 1.16 mmol, 80.27 μL) was added to the reaction solution under stirring. At last, the reaction solution was stirred under nitrogen atmosphere at 15-20° C. for 45 minutes. The reaction solution was directly rotary-evaporated to dryness to obtain a crude product. The crude product was purified by high-performance liquid chromatography (with TFA system) to obtain Comparative Compound 3. The Comparative Compound 3 can be dissolved in dichloromethane and then washed with 1N sodium bicarbonate to obtain the free base.

LCMS (ESI) m/z: 429.2 [M+H]⁺

¹H NMR (400 MHz, CD₃OD) δ 9.03 (s, 1H), 8.90 (d, J=6.8 Hz, 1H), 8.29-8.34 (m, 1H), 7.60 (s, 1H), 7.44-7.68 (m, 1H), 7.03 (d, J=6.0 Hz, 2H), 4.21 (s, 3H), 2.63-2.68 (m, 1H), 0.79-0.80 (m, 2H), 0.55 (s, 2H).

Process C

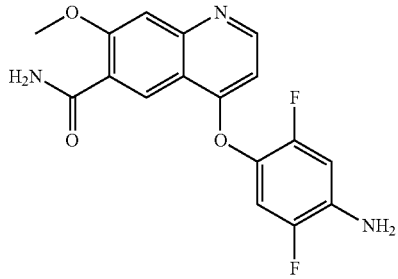 [SMILES: COc1cc2nccc(Oc3cc(F)c(N)cc3F)c2cc1C(N)=O]

-continued

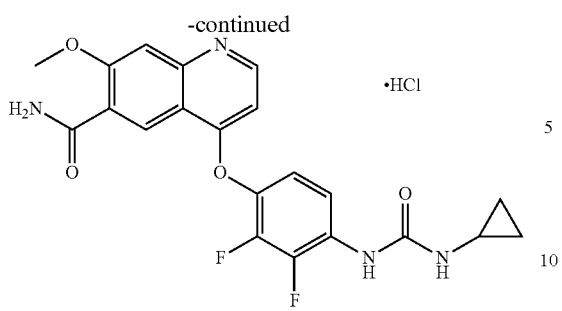

Comparative Embodiment 4A

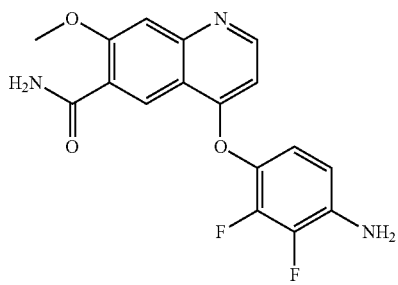 [SMILES: COc1cc2nccc(Oc3ccc(N)c(F)c3F)c2cc1C(N)=O]

The Comparative Embodiment 4A adopts the preparation method of the Comparative Embodiment 3A to obtain the product.

LCMS (ESI) m/z: 346.1 [M+H]+

$^1$H NMR (400 MHz, CD$_3$OD) δ 8.66-8.73 (m, 2H), 7.80 (s, 1H), 7.76 (s, 1H), 7.49-7.57 (m, 1H), 7.02 (t, J=8.0 Hz, 1H), 6.68 (t, J=8.0 Hz, 1H), 6.49-6.54 (m, 1H), 5.63 (s, 2H), 4.03 (s, 3H).

Comparative Embodiment 4

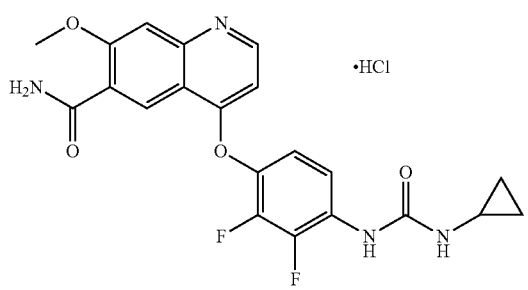 [SMILES: COc1cc2nccc(Oc3ccc(NC(=O)NC4CC4)c(F)c3F)c2cc1C(N)=O ; Cl]

Triphosgene (34.38 mg, 115.84 μmol) was added to the mixture of the product of Embodiment 1A (200 mg, 579.21 μmol) and triethylamine (175.83 mg, 1.74 mmol, 241.86 μL) in dichloromethane (5 mL), and the mixture was stirred under nitrogen protection at 15-20° C. for 15 minutes. Then cyclopropylamine (66.14 mg, 1.16 mmol, 80.27 μL) was added to the reaction solution under stirring. At last, the reaction solution was stirred under nitrogen atmosphere at 15-20° C. for 45 minutes. The reaction solution was directly rotary-evaporated to dryness to obtain a crude product. The crude product was purified by high performance liquid chromatography (under HCl condition) to obtain Comparative Compound 4 as the final product. The Comparative Compound 4 can be dissolved in dichloromethane and washed with 1N sodium bicarbonate to obtain the free base.

LCMS (ESI) m/z: 429.2 [M+H]+

$^1$H NMR (400 MHz, CD$_3$OD) δ 9.05 (s, 1H), 8.97 (d, J=6.8 Hz, 1H), 8.07 (s, 1H), 7.65 (s, 1H), 7.30-7.34 (m, 1H), 7.16 (d, J=6.8 Hz, 2H), 4.24 (s, 3H), 2.63-2.68 (m, 1H), 0.78-0.82 (m, 2H), 0.57 (s, 2H)

Process D

Process D

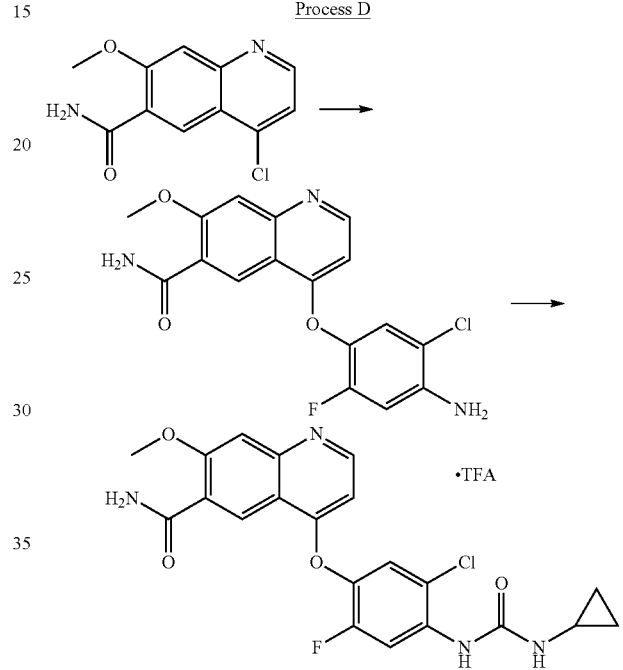

Comparative Embodiment 5A

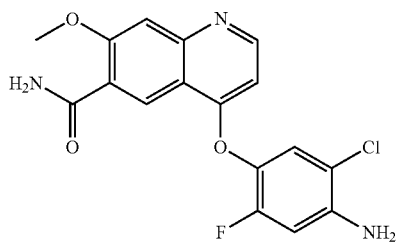 [SMILES: COc1cc2nccc(Oc3cc(Cl)c(N)cc3F)c2cc1C(N)=O]

Cs$_2$CO$_3$ (550.71 mg, 1.69 mmol) was added to a solution of 4-chloro-7-methoxyquinoline-6-formamide (200 mg, 845.12 μmol) and 4-amino-5-chloro-2-fluorophenol (341.35 mg, 2.11 mmol) in N-methyl pyrrolidone (2 mL), and the mixture was heated to 140° C. and reacted for 2 hours under microwave conditions. LCMS (es8146-386-p1a) detection showed that some of the raw materials were not completely consumed. The reaction solution was slowly added dropwise to ice water (10 mL), and a large amount of solids were precipitated. The mixture was filtered, and the filter cake was rotary-evaporated under vacuum to dryness to obtain a product of Comparative Embodiment 5A. LCMS (ESI) m/z: 384.1 [M+23]+

Comparative Embodiment 5

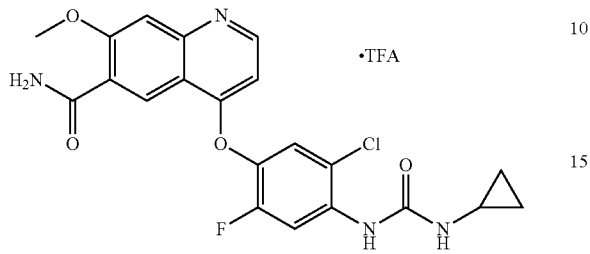

The product of Comparative Embodiment 5A (50 mg, 138.22 µmol) was added to dichloromethane (5 mL). Triphosgene (32.81 mg, 110.57 µmol) and diisopropylethylamine (DIEA, 53.59 mg, 414.65 µmol, 72.22 µL) were added to the reaction solution under stirring, the reaction was carried out at 15-20° C. for 15 minutes under stirring, cyclopropylamine (15.78 mg, 276.43 µmol, 19.15 µL) was added to the reaction solution, and the reaction solution was continuously stirred at room temperature for 30 minutes. LCMS detection showed that the raw materials were completely consumed. The reaction solution was directly concentrated under reduced pressure to give a crude product, which was purified by high-performance liquid chromatography (under TFA condition) to obtain Comparative Compound 5. The Comparative Compound 5 can be dissolved in dichloromethane and washed with 1N sodium bicarbonate to obtain the free base.

LCMS (ESI) m/z: 467.1 [M+23]+

$^1$H NMR (400 MHz, METHANOL-$d_4$) δ ppm 9.03 (s, 1H) 8.89 (d, J=6.52 Hz, 1H) 8.39 (d, J=13.30 Hz, 1H) 7.68 (d, J=8.03 Hz, 1H) 7.60 (s, 1H) 7.01 (d, J=7.03 Hz, 1H) 4.21 (s, 3H) 2.61-2.72 (m, 1H) 0.50-0.86 (m, 4H)

Process E

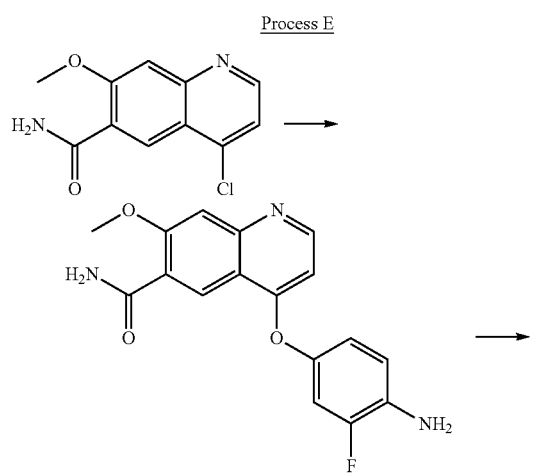

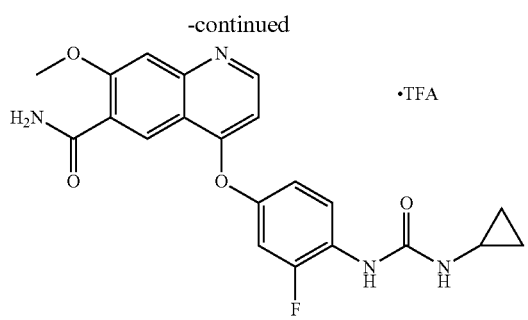

Comparative Embodiment 6A

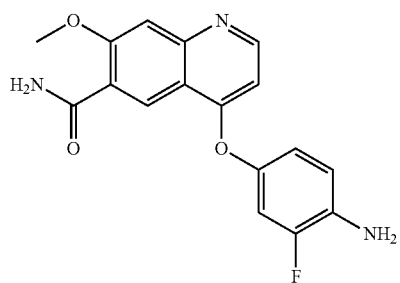 [SMILES: COc1cc2nccc(Oc3ccc(N)c(F)c3)c2cc1C(N)=O]

The Comparative embodiment 6A adopts the preparation method of the Comparative embodiment 5A to obtain a product.

LCMS (ESI) m/z: 328.2 [M+1]+

Comparative Embodiment 6

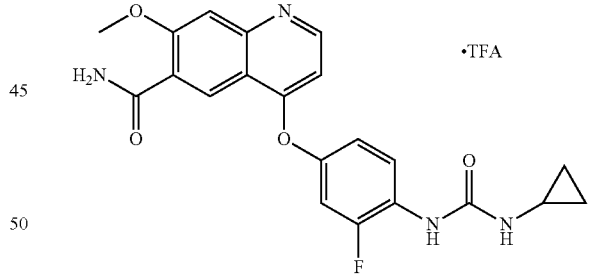

The product of Comparative Embodiment 6A (50 mg, 152.76 µmol) was added to dichloromethane (5 mL), and triphosgene (36.27 mg, 122.21 µmol) and DIEA (59.23 mg, 458.28 µmol, 79.82 µL) were added to the reaction solution under stirring, and the reaction was carried out at 15-20° C. under stirring for 15 minutes. Cyclopropylamine (17.44 mg, 305.52 µmol, 21.17 µL) was added to the reaction solution, and the reaction solution was continuously stirred at room temperature for 30 minutes. LCMS detection showed that the raw materials were completely consumed. The reaction solution was directly concentrated under reduced pressure to obtain a crude product. The crude product was purified by high-performance liquid chromatography (under TFA condition) to obtain Comparative Compound 6. The Comparative Compound 6 can be dissolved in dichloromethane and then washed with 1N sodium bicarbonate to obtain the free base.

LCMS (ESI) m/z: 411.0 [M+1]$^+$ $^1$H NMR (400 MHz, CD$_3$OD) δ ppm 9.12 (s, 1H) 8.38 (d, J=7.03 Hz, 1H) 7.54 (t, J=8.66 Hz, 1H) 7.41 (s, 1H) 7.25-7.33 (m, 1H) 7.19 (br d, J=8.78 Hz, 1H) 6.61 (br d, J=5.27 Hz, 1H) 4.18 (s, 3H) 0.55-0.90 (m, 4H)

Process E

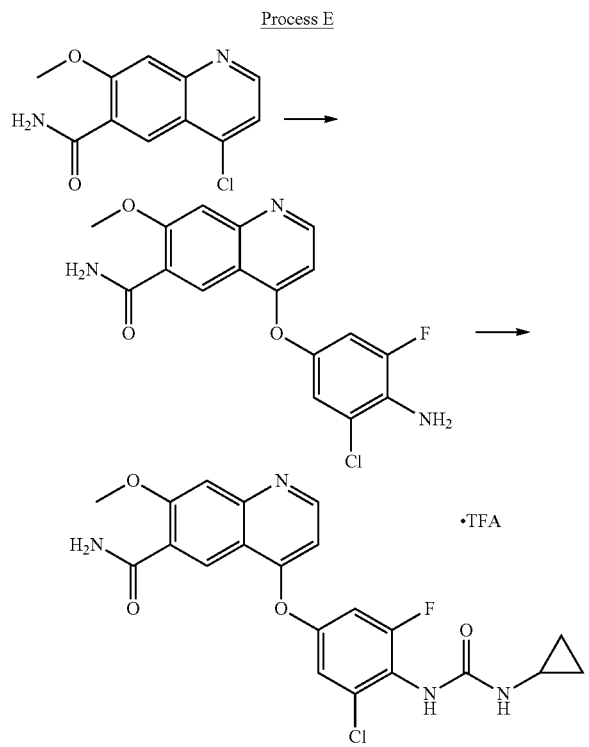

Process E

Comparative Embodiment 7A

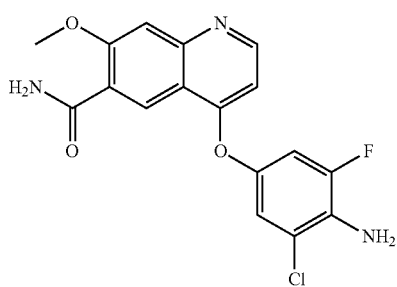 [SMILES: COc1cc2nccc(Oc3cc(F)c(N)c(Cl)c3)c2cc1C(N)=O]

The Comparative Embodiment 7A adopts the preparation method of the Comparative Embodiment 3A to obtain a product.

LCMS (ESI) m/z: 362.1 [M+H]$^+$

Comparative Embodiment 7

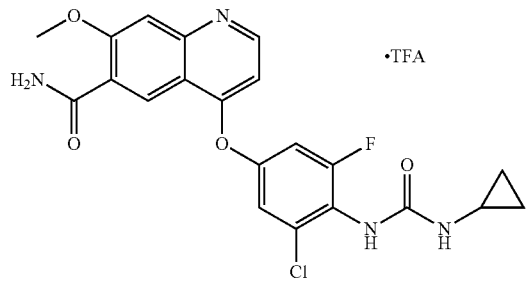 [SMILES: COc1cc2nccc(Oc3cc(F)c(NC(=O)NC4CC4)c(Cl)c3)c2cc1C(N)=O ; "·TFA"]

Triphosgene (34.38 mg, 115.84 μmol) was added to the mixture of the product of Comparative Embodiment 7A (50 mg, 138.22 μmol) and triethylamine (41.96 mg, 414.65 μmol, 57.71 μL) in dichloromethane (2 mL), and the mixture was stirred under nitrogen atmosphere at 15-20° C. for 10 minutes. Then cyclopropylamine (15.78 mg, 276.43 μmol, 19.15 μL) was added to the reaction solution under stirring. At last, the reaction solution was allowed to react under stirring and nitrogen atmosphere at 15-20° C. for 50 minutes. The reaction solution was directly rotary-evaporated to dryness to obtain a crude product, which was purified by high performance liquid chromatography (under TFA condition) to finally obtain Comparative Compound 7, which was subjected to LCMS and NMR detections. The Comparative Compound 7 can be dissolved in dichloromethane and then washed with 1N sodium bicarbonate to obtain the free base.

LCMS (ESI) m/z: 445.2 [M+H]$^+$ $^1$H NMR (400 MHz, CD$_3$OD) δ 8.94 (s, 1H), 8.72 (d, J=5.2 Hz, 1H), 7.56 (s, 1H), 7.34 (m, 1H), 7.20-7.24 (m, 1H), 6.90 (d, J=5.2 Hz, 1H), 4.15 (s, 3H), 2.62-2.68 (m, 1H), 0.80-0.81 (m, 2H), 0.61 (s, 2H)

Biological Test Data:

Experimental Embodiment 1: In Vitro Enzyme Activity Test of the Compounds of the Present Disclosure Experimental Objective The enzyme activity was detected by Z'-LYTE™ Detection Kinase Assay, and the inhibition effects of Compound 1B, Lenvatinib and Comparative Compound 2 on seventeen kinases including ABL, c-Met, TNIK, FGFR1-4, Flt1, Flt4, KDR, MINK, LCK, cKIT, PDGFRα, PDGFRβ, cKit (V560G) were evaluated by the IC$_{50}$ values of the compounds as indexes.

Experimental Method

The compounds were subjected to four-fold serial dilution when evaluated on c-Met, FGFR1, and FGFR4 kinases, and the concentrations thereof were 10 μM to 0.038 nM; the compounds were subjected to three-fold serial dilution when evaluated on other kinases, the final concentrations thereof included 9 concentrations from 10 μM to 1 nM, and each concentration was repeated in two wells; the DMSO content in the reaction to be detected was 2%.

General Enzyme Reaction Procedure:

Protein kinase with a corresponding enzyme concentration of X (shown in table 1), peptide substrate with a concentration of Y, ATP with a specific concentration, 8 mM MOPS (pH 7.0), and 10 mM $MgCl_2$ were added. The detection plate was P30 filtermat, and the reaction was performed at room temperature for T minutes, and the reaction system was 10 µL.

TABLE 1

Conditions for kinase test

| Kinase | Enzyme concentration (X) (nM) | Tyr peptide (Y) | ATP concentration (µM) | Reaction time (T) (min) |
|---|---|---|---|---|
| Abl(h) | 7.65 | 50 µM | 10 | 40 |
| c-Met | 8 | 20 µM | 10 | 120 |
| TNIK(h) | 8.65 | 250 µM | 10 | 40 |
| FGFR1(h) | 1.75 | 0.2 mg/mL | 5 | 120 |
| FGFR2(h) | 2.99 | 0.1 mg/mL | 10 | 40 |
| FGFR3(h) | 13.03 | 0.1 mg/mL | 10 | 40 |
| FGFR4(h) | 2.5 | 0.2 mg/mL | 100 | 120 |
| Flt1(h) | 157.27 | 250 µM | 10 | 40 |
| Flt4(h) | 64.91 | 500 µM | 10 | 40 |
| KDR(h) | 55.23 | 0.33 mg/mL | 10 | 40 |
| MINK(h) | 35.40 | 0.33 mg/mL | 10 | 40 |
| Lck(h) | 366.10 | 250 µM | 10 | 40 |
| cKit(h) | 383.75 | 0.1 mg/mL | 10 | 40 |
| PDGFRα(h) | 270.87 | 0.1 mg/mL | 10 | 40 |
| PDGFRβ(h) | 310.83 | 0.1 mg/mL | 10 | 40 |
| cKit(V560G)(h) | 83.44 | 250 µM | 10 | 40 |
| Aurora-A(h) | 3.08 | 200 µM | 10 | 40 |

Reaction Detection:

The reaction was terminated by adding 0.5% phosphoric acid to the kinase reaction solution, and the plate was read by an Envision instrument.

Data Analysis

The data were converted into phosphorylation rate and inhibition rate, and subjected to parameter curve-fitting (GraphPad Software) to obtain $IC_{50}$ data of the compounds.

The experimental results are shown in Table 2:

TABLE 2 main kinase activity $IC_{50}$ test results of the product of Embodiment 1B and Comparative Compounds

| | Embodiment 1B $IC_{50}$(nM) | Comparative Compound 1 (Lovatinib) $IC_{50}$ (nM) | Comparative Compound 2 $IC_{50}$ (nM) |
|---|---|---|---|
| Abl(h) | 7 | 36 | 520 |
| c-Met | 99.8 | 598 | NA |
| TNIK(h) | 14 | 91 | 118 |
| FGFR1(h) | 9 | 76.6 | 69 |
| FGFR2(h) | 6 | 14 | 15 |
| FGFR3(h) | 26 | 132 | 132 |
| FGFR4(h) | 92 | 1120 | 131 |
| Flt1(h) | 10 | 13 | 31 |
| Flt4(h) | 3 | 3 | 8 |
| KDR(h) | 9 | 7 | 7 |
| MINK(h) | 48 | 359 | 55 |
| Lck(h) | 43 | 69 | 252 |
| cKit(h) | 68 | 78 | NA |
| PDGFRα(h) | 120 | 129 | 135 |
| PDGFRβ(h) | 226 | 275 | 31 |
| cKit(V560G)(h) | 262 | 596 | NA |
| Aurora-A(h) | 2079 | 2937 | 262 |

NA: untested.

TABLE 3

FGFR1, FGFR4 and VEGFR2 kinase activity $IC_{50}$ (nM) test results of the product of Embodiment 1B and Comparative Compounds

| | FGFR1(h) | FGFR4(h) | c-Met | ABL (h) |
|---|---|---|---|---|
| Comparative Compound 1B | 9 | 92 | 45.6[Note 1] | 7 |
| Comparative Compound 3 | 160 | 509 | >10,000 | 817 |
| Comparative Compound 4 | 31 | 108 | 79.8 | 292 |
| Comparative Compound 5 | 89 | 137 | 32 | 207 |
| Comparative Compound 6 | 1744 | 4557 | 282 | 2210 |
| Comparative Compound 7 | 54 | 1115 | >10,000 | NA |

Note [1] the second test
NA: untested.

Experimental Conclusion

In table 2, compared with Comparative Compound 1, the product of Embodiment 1B significantly increased the activity on multiple kinases, wherein the activity on c-Met was increased by 5 times, the activity on TNIK was increased by 6.5 times, and the activity on ABL was increased by 5 times, and significantly increased the activity on each subtype of FGFR, wherein the activity on FGFR1 was increased by 8 times, the activity on FGFR2 was increased by 2 times, the activity on FGFR3 was increased by 5 times, and the activity on FGFR4 was increased by 12 times.

Compound 1B have better tumor treatment effect due to the improvement of the activities on these important targets, especially, the improvement of the activities on FGFR and c-Met, which will produce a better therapeutic effect in patients with gastric cancer, lung cancer and the like with high expression of FGFR and c-Met. Compared with Comparative Compound 2, the product of Embodiment 1B greatly improved the activity on ABL by nearly 70 times and the activity on TNIK by 8 times, which is unexpected, and thus the compound can have a better therapeutic effect in cancers with gene fusion such as BCR-ABL.

Table 3 shows that, the product of Embodiment 1B with fluorine and chlorine located on the same side of the benzene ring significantly improved inhibitory activities on FGFR1, FGFR4 and ABL kinases, compared with Comparative Compounds 3, 4, 5, 6, and 7 with fluorine and chlorine located on other positions.

Experimental Embodiment 2: Pharmacokinetic Evaluation of Compounds

Experimental objective: evaluation of the oral absorption in animals of the product of Embodiment 1 by intravenous and oral administration in mice Experimental materials: Balb/c nude mice, EDTA-K2

Experimental Operation:

Experimental procedure: 0.5 mg/mL 5% DMSO/95% (10% HP-β-CD) clear solution of the product of Embodiment 1 was injected intravenously into male Balb/c nude mice (overnight fasting, 7-9 week-age) via caudal vein at a dose of 1 mg/kg. 0.5 mg/mL test compound suspended in 0.5% Methocel/0.2% Tween 80 was administered intragastrically to male Balb/c nude mice (overnight fasting, 7-9 week-age) at a dose of 5 mg/kg. About 30 µL blood was collected from the jugular or caudal vein of each animal in the two groups at 0.25, 0.5, 1.0, 2.0, 4.0, 8.0 and 24 hours after administration, added into anticoagulated tubes containing EDTA-K2, and the mixture was centrifuged to obtain the plasma. LC-MS/MS method was used to determine the drug concentration in blood, and WinNonlin™ Version 6.3 (Pharsight, Mountain View, Calif.) pharmacokinetic software was used to calculate the relevant pharmacokinetic parameters by non-compartment model logarithmic trapezoidal method.

Experimental Results:

After single administration by intravenous injection to the male Balb/c nude mice at a dose of 1.0 mg/kg, the product of Embodiment 1 has a plasma clearance (CL) of 11 mL/min/kg and an apparent volume of distribution at steady state (Vdss) of 1.48 L/kg, elimination half-life ($T_{1/2}$) value of 2.68 h, and the area under the plasma concentration-time curve from time 0 point to the last quantifiable time point ($AUC_{0-last}$) of 3213 nM·h.

After a single intragastric administration to male Balb/c nude mice at a dose of 5 mg/kg, the product of Embodiment 1 has a bioavailability of 144%, an $AUC_{0-last}$ of 24899 nM·h, a peak concentration ($C_{max}$) of 9825 nM, and the time to peak concentration was 0.5 h after the administration.

Experimental Embodiment 3: Pharmacokinetic Evaluation of Compounds

Experimental objective: evaluation of the oral absorption in animals of the product of Embodiment 1 by intravenous and oral administration in rats Experimental materials: male, SD rats, EDTA-K2

Experimental Operation:

Experimental procedure: 0.5 mg/mL 5% DMSO/95% (10% HP-β-CD) clear solution of the product of Embodiment 1 or Comparative Compound 1 was injected intravenously into male SD rats (overnight fasting, 7-11 week-age) via caudal vein at a dose of 1 mg/kg. 0.5 mg/mL of the test compound suspended in 0.5% Methocel/0.2% Tween 80 was administered intragastrically to male SD rats (overnight fasting, 7-11 week-age) at a dose of 5 mg/kg. About 30 µL blood was collected from the jugular or caudal vein of each animal in the two groups at 0.25, 0.5, 1.0, 2.0, 4.0, 8.0, and 24 hours after administration, added into anticoagulated tubes containing EDTA-K2, and the mixture was centrifuged to obtain the plasma. LC-MS/MS method was used to determine the drug concentration in blood, and WinNonlin™ Version 6.3 (Pharsight, Mountain View, Calif.) pharmacokinetic software was used to calculate the relevant pharmacokinetic parameters by non-compartment model logarithmic trapezoidal method.

Experimental Results:

Embodiment 1

After single administration by intravenous injection to the male SD rats at a dose of 1.0 mg/kg, the product of embodiment 1 has a plasma clearance (CL) of 1.6 mL/min/kg, an apparent volume of distribution at steady state (Vdss) of 0.259 L/kg, an elimination half-life ($T_1/2$) value of 2.64 h and an area under the plasma concentration-time curve from time 0 point to the last quantifiable time point ($AUC_{0-last}$) of 23441 nM·h.

After a single intragastric administration to male SD rats at a dose of 5 mg/kg, the product of embodiment 1 has a bioavailability of 60.8%, an $AUC_{0-last}$ of 71053 nM·h, a peak concentration ($C_{max}$) of 19600 nM, and the time to peak concentration was 0.375 h after the administration.

Comparative Compound 1:

After single administration by intravenous injection to the male SD rats at a dose of 1.0 mg/kg, Comparative Compound 1 has a plasma clearance (CL) of 2.6 mL/min/kg, an apparent volume of distribution at steady state (Vdss) of 0.407 L/kg, an elimination half-life ($T_{1/2}$) value of 2.53 h, and an area under the plasma concentration curve from time 0 point to the last quantifiable time point ($AUC_{0-last}$) of 15149 nM·h.

After a single intragastric administration to male SD rats at a dose of 5 mg/kg, Comparative Compound 1 has a bioavailability of 58.7%, an area under plasma concentration-time curve ($AUC_{0-last}$) of 44476 nM·h, a peak concentration ($C_{max}$) of 10095 nM, and the time to peak concentration was 1.25 h after the administration.

Compared with Comparative Compound 1, the pharmacokinetic data on rats shows that the product of Embodiment 1 has a plasma clearance reduced by about: (2.6−1.6)/2.6*100%=38%, an area under the plasma drug concentration-time curve ($AUC_{0-last}$) significantly increased by: (23441-15149)/15149*100%=55% for intravenous administration; and an area under the plasma drug concentration-time curve ($AUC_{0-last}$) significantly increased by: (71053−44476)/44476*100%=27% for oral absorption.

Conclusion: in mice and rat species, the product of Embodiment 1 of the present disclosure has low clearance rate, high oral bioavailability, and excellent druggability. Compared with Compared Compound 1 (commercially available drug Lovatinib), the introduction of F atom on the benzene ring of the quinoline core structure significantly reduces the drug metabolism rate in rats and significantly increases the oral absorption of the drug.

What is claimed is:

1. A compound represented by formula (II) or a pharmaceutically acceptable salt thereof,

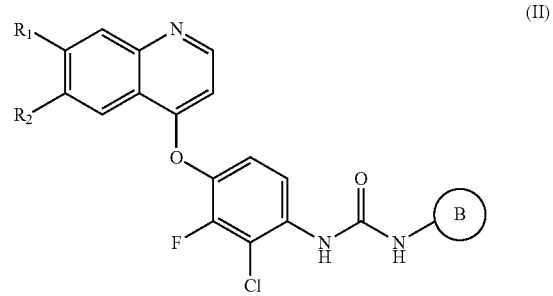

wherein,
$R_1$ is $C_{1-6}$ alkoxy optionally substituted by 1, 2 or 3 R;
$R_2$ is selected from the group consisting of —C(=O)NH$_2$ and —C(=O)NH—$C_{1-3}$ alkyl;
ring B is $C_{3-6}$ cycloalkyl;
R is selected from the group consisting of F, Cl, Br, I, OH and NH$_2$.

2. The compound or the pharmaceutically acceptable salt thereof as defined in claim 1, wherein $R_1$ is

3. The compound or the pharmaceutically acceptable salt thereof as defined in claim 1, wherein $R_2$ is —C(=O)NH$_2$.

4. The compound or the pharmaceutically acceptable salt thereof as defined in claim 1, wherein ring B is cyclopropyl.

5. The compound or the pharmaceutically acceptable salt thereof as defined in claim 1, wherein the compound is (II-1)

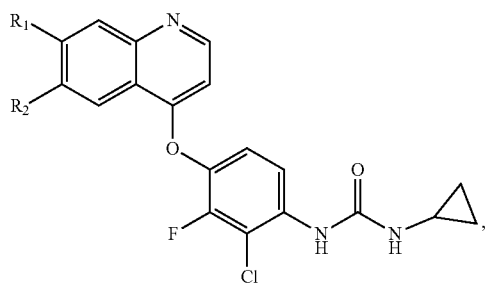

wherein $R_1$ and $R_2$ are as defined in claim 1.

6. A compound represented by the following formula or a pharmaceutically acceptable salt thereof:

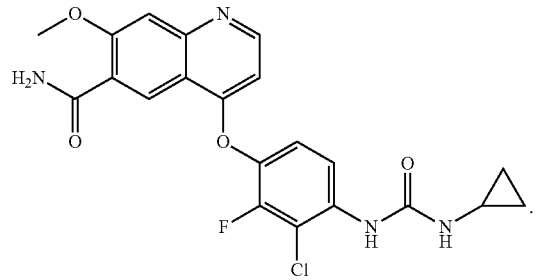 [SMILES: COc1cc2nccc(Oc3ccc(NC(=O)NC4CC4)c(Cl)c3F)c2cc1C(N)=O]

7. A method for treating a disease associated with tyrosine kinase inhibitor in a subject in need thereof, wherein the disease associated with tyrosine kinase inhibitor is tumor disease or immune disorder, comprising: administering an effective amount of the compound or the pharmaceutically acceptable salt thereof as defined in claim 1 to the subject.

8. A pharmaceutical composition comprising the compound or the pharmaceutically acceptable salt thereof as defined in claim 1 and a pharmaceutically acceptable carrier.

9. A method for treating a disease associated with tyrosine kinase inhibitor in a subject in need thereof, wherein the disease associated with tyrosine kinase inhibitor is tumor disease or immune disorder, comprising administering an effective amount of the pharmaceutical composition as defined in claim 8 to the subject.

* * * * *